United States Patent [19]

Floc'H et al.

[11] Patent Number: 5,459,263
[45] Date of Patent: Oct. 17, 1995

[54] MEDICINAL PRODUCTS AND PURE PREPARATIONS OF MELARSOMINE DIHYDROCHLORIDE, PROCESS FOR OBTAINING THEM AND INTERMEDIATE PRODUCTS OBTAINED

[75] Inventors: Robert Floc'H, Plaisance du Touch; Jean-Pierre Etchegaray, Toulouse Saint-Simon; Gérard Wolf, Toulouse; Patrick Lubert, Artois; Régine J. A. Mazars, Ramonville Saint-Agne, all of France

[73] Assignee: Rhone Mereiux, Lyons, France

[21] Appl. No.: 984,934

[22] Filed: Dec. 2, 1992

[30] Foreign Application Priority Data

Dec. 2, 1991 [FR] France .................... 91 14904

[51] Int. Cl.⁶ .............................. C07D 251/70
[52] U.S. Cl. .......................... 544/181; 544/180
[58] Field of Search ................ 544/181; 514/184

[56] References Cited

U.S. PATENT DOCUMENTS

| | | | |
|---|---|---|---|
| 2,295,574 | 9/1942 | Friedheim | 544/181 |
| 2,386,204 | 10/1945 | Friedheim | 260/242 |
| 2,390,091 | 6/1944 | Friedheim | 544/181 |
| 2,400,547 | 5/1946 | Friedheim | 260/242 |
| 2,422,724 | 6/1947 | Friedheim | 260/242 |
| 2,593,434 | 4/1950 | Friedheim | 167/69 |
| 2,659,723 | 11/1953 | Friedheim | 260/242 |
| 2,659,723 | 11/1953 | Friedheim | 260/242 |
| 3,482,171 | 12/1969 | Himes et al. | 328/155 |
| 3,856,971 | 12/1974 | Friedheim et al. | 424/297 |
| 3,974,148 | 8/1976 | Friedheim et al. | 260/242 |
| 4,456,610 | 6/1984 | Hofheinz et al. | 424/273 R |
| 4,514,390 | 4/1985 | Friedheim | 514/184 |

FOREIGN PATENT DOCUMENTS

| | | |
|---|---|---|
| 0006752 | 9/1980 | European Pat. Off. |
| 214345 | 7/1941 | Switzerland |

OTHER PUBLICATIONS

Banks et al. J. Amer. Chem. Soc., Oct. 1944, p. 1771 vol. 66.
Journal of American Chemical Society, 1944, 66, 1771.

*Primary Examiner*—Mukund J. Shah
*Assistant Examiner*—P. K. Sripada
*Attorney, Agent, or Firm*—Larson and Taylor

[57] ABSTRACT

The medicinal product comprises as active principle a melarsomine hydrochloride preparation having a purity of between 98.5 and 100%. The process for obtaining this preparation is stated essentially as follows:

step 1, trichlorotriazine (TCT) is converted to diaminochlorotriazine (DCT) in an ammoniacal medium;

step 2, the DCT is converted to melarsen acid hydrochloride (MAH) in the presence of arsanilic acid;

step 3, the MAH is reduced to melarsen oxide dihydrate; and step 4, the melarsen oxide dihydrate is converted to melarsomine dihydrochloride in the presence of cysteamine hydrochloride. In each step, a purified preparation of the corresponding intermediate product, or final product in step 4, is obtained.

15 Claims, 2 Drawing Sheets

MEDICINAL PRODUCTS AND PURE PREPARATIONS OF MELARSOMINE DIHYDROCHLORIDE, PROCESS FOR OBTAINING THEM AND INTERMEDIATE PRODUCTS OBTAINED

The invention relates to medicinal products comprising pure preparations of melarsomine dihydrochloride as active principle, in particular as an antiparasitic and more especially macrofilaricidal and trypanocidal agent.

The invention also relates to a new process for the synthesis of melarsomine dihydrochloride, and to the pure preparations of melarsomine dihydrochloride and of intermediate products obtained in this process.

Organoarsenic derivatives are known as macrofilaricidal and trypanocidal agents. A large number of organoarsenic derivatives have been synthesised and tested in different forms, such as, for example, the compounds described in U.S. Pat. No. 2,659,723.

Organoarsenic derivatives, melaminylthioarsenates, form the subject of U.S. Pat. No. 4,514,390, including cysteamine melaminylthioarsenate dihydrochloride or melarsomine dihydrochloride, bis(2-aminoethyl) 4-[(4,6-diamino-1,3,5-triazin-2-yl)amino]phenyldithioarsonire hydrochloride, of formula:

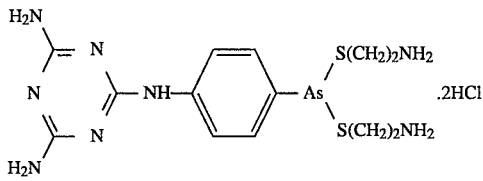

This derivative is obtained by reacting melarsen oxide dihydrate or arsenone and cysteamine hydrochloride together in an ethanolic medium at the boiling point (Example 1 of U.S. Pat. No. 4,514,390 cited above).

According to U.S. Pat. No. 2,295,574, diaminochlorotriazine (DCT) may be used for the synthesis of arsenical compounds. DCT was synthesised for the first time by Liebig (Annalen der Pharmazie, Volume 10, 1834, page 43).

Moreover, trichlorotriazine (TCT) also constitutes a known starting point for the synthesis of arsenical compounds. Thus, according to U.S. Pat. No. 295,574, it is known to synthesise melarsen acid hydrochloride (MAH) starting from 2,4,6-trichloro-1,3,5-triazine, which is reacted with arsanilic acid in an aqueous medium, and the reaction product is then converted to MAH in the presence of ammonia solution and. hydrochloric acid at between 110° and 130° C.

According to U.S. Pat. No. 2,390,091, MAH can itself be used in condensation reactions to synthesise substituted 1,3,5-triazinyl-(6)-aminophenyl arsenical compounds.

Apart from the degree of efficacy of the arsenical derivatives, the two main problems are tolerance with respect to the active principle and the mode of administration. In effect, most arsenical derivatives in subcutaneous or intramuscular injection cause inflammations or necroses, and they should hence preferably be administered intravenously.

The process according to U.S. Pat. No. 4,514,390 cited above makes use of an excess of thiol in an attempt to bring about the most complete possible reaction and hence to decrease to the maximum extent the amount of toxic melarsen oxide dihydrate in the final product.

Other considerable drawbacks lie in the synthesis processes, namely, in particular, the presence of substantial reaction residues which must necessarily be eliminated, requiring costly steps of purification and then of treatment of the mother liquors. and effluents therefrom.

Thus, the objective of the present invention is to provide new medicinal products based on melarsomine dihydrochloride preparations of high purity, capable of being administered by various routes including the intramuscular and subcutaneous routes.

Another objective of the invention is to provide a process for the production of these pure preparations, and in particular such a process possessing optimised reaction conditions in order, in particular, to yield intermediate products of high purity and to limit to the maximum extent the reaction residues and thus the purification phases and the volume of the mother liquors therefrom.

Thus, the subject of the present invention is a medicinal product comprising as active principle a preparation of melarsomine dihydrochloride, the preparation having per sea purity of between 98.5 and 100%.

The medicinal product according to the invention is preferably in lyophilised form, to be redissolved at the time of use. The assay of the solution remains stable for at least 72 hours at 4° C. protected from light. A standard lyophilisation stabiliser, for example glycine, may optionally be combined therewith.

The subject of the present invention is also a process that permits the production of preparations according to the invention for making the abovementioned medicinal products, characterised in that:

step 1, trichlorotriazine (TCT) is converted to diaminochlorotriazine (DCT) in an ammoniacal medium;

step 2, the DCT is converted to melarsen acid hydrochloride (MAH) in the presence of arsanilic acid;

step 3, the MAH is reduced to melarsen oxide dihydrate; and step 4, the melarsen oxide dihydrate is converted to melarsomine dihydrochloride in the presence of cysteamine hydrochloride.

Preferably, in step 1: the TCT is reacted with an ammonia solution in two substeps, the first comprising the gradual addition of TCT to the ammonia solution under conditions that limit the reaction temperature to below approximately 20° C., and preferably to a temperature of the order of 0° to 5° C. approximately, throughout this first substep, while, in the second substep, the reaction is completed by bringing the temperature of the solution obtained to between 20° and 90° C. approximately, and preferably to approximately 40° C., and the diaminochlorotriazine (DCT) obtained is then purified by washing with hot water, in particular by resuspension in hot water, in particular in water at 90°–95° C. approximately, to solubilise the impurities.

Preferably:

step 2: in an aqueous medium, the DCT is converted to melarsen acid hydrochloride in the presence of arsanilic acid, and the MAH is then precipitated in an acid medium;

step 3: the melarsen acid hydrochloride, previously dried or otherwise, is reduced in an aqueous or preferably an organic medium, such as the alcohols tertiary butanol, isopropanol, ethanol, methanol, or in an aqueous-alcoholic medium, in the presence of a reducing agent such as $SOCl_2$, $NaHSO_2$, $H_2SO_3$ or $SO_2$ and optionally of traces of potassium iodide, in the presence of acid or otherwise, to give melarsen oxide dihydrate, which is then dried or otherwise;

step 4: the dry or wet melarsen oxide dihydrate is suspended in water and then brought into contact with cysteamine hydrochloride to give melarsomine dihydrochloride, which may thereafter be recovered in solid form by crystallisation at low temperature or the like, followed by drying. Advantageously, the sterile melarsomine dihydrochloride may be recovered by lyophilisation and packaged.

As a variant, the process for the synthesis of cysteamine melaminylthioarsenate dihydrochloride or melarsomine dihydrochloride, in which the latter is prepared from trichlorotriazine (TCT), proceeding via diaminochlorotriazine (DCT), then melarsen acid hydrochloride (MAH) and then melarsen oxide dihydrate, comprises at least one of the abovementioned steps 1 to 4.

It is of great importance that the DCT used in step 2 is of high purity if it is desired to decrease the formation of impurities in the following steps, these conditions also being necessary for obtaining a final product of suitable purity. The process according to the invention as a whole makes it possible very advantageously to dispense with the customary steps of purification of arsenical derivatives which generate large volumes of mother liquors requiring treatment. Intermediate reaction products of high purity, a condition of the synthesis of a very pure melarsomine dihydrochloride, and large gains in productivity and in yield are the consequences thereof.

According to the invention:

step 2 may advantageously be performed at a temperature of between 0° and 95° C., until dissolution of the arsanilic acid is complete, which may be assessed by the change in the turbidity of the solution;

step 3 may advantageously be performed at a temperature of the order of 10° to 60° C. or 65° C., and in particular 30° to 40° C., with a gradual injection of $SO_2$ as reducing agent in the proportion of 4.4 to 20 g, and in particular 12 to 15 g, approximately of $SO_2$ per 25 g of melarsen acid, until a homogeneous medium is obtained;

step 4 may advantageously be carried out at a temperature of between 20° and 100° C. approximately, in particular between 40° and 50° C. and especially at approximately 40° C., until dissolution of the melarsen oxide dihydrate is complete. Advantageously, step 4 is performed with approximately 1 mol of melarsen oxide dihydrate per 2 mol of cysteamine hydrochloride.

Advantageously, step 3 is performed in a volume of 100 to 200 ml approximately of methanol. per 10 to 60 g approximately of dry or wet melarsen acid, and in particular approximately 25 g.

Preferably, in step 1, from 30 to 200 g approximately, and in particular from 50 to 70 g approximately, of TCT are reacted per litre of ammonia solution containing, in particular, from 5 to 28% weight/weight approximately of $NH_3$, and in particular from 15 to 20% weight/weight. For reasons of heat transfer and of viscosity of the medium, it is advantageous to work with between 50 to 70 g of TCT per litre of ammonia solution.

The TCT is advantageously introduced over a period of more than 40 min, and in particular of approximately 120 min, in continuous or discontinuous fashion, into the ammonia solution whose initial temperature is between 0° and 20° C. approximately, and in particular between 0° and 5° C. approximately, it being necessary for the temperature to be maintained in this range throughout the operation.

In the second substep of step 1, the solution is preferably heated to between 20° and 90° C. approximately for from 10 to 180 min approximately, and preferably to approximately 40° C. for approximately 90 min.

This synthesis process makes it possible to obtain a melarsomine dihydrochloride having a purity of greater than 98.5% and which can reach 100%, which is capable of being administered by various routes such as the oral, intravenous, intramuscular and subcutaneous routes.

The subject of the invention is hence also the melarsomine dihydrochloride preparations obtained by the process according to the invention, having a purity of between 98.5% and 100%.

The subject of the invention is also the melarsomine dihydrochloride preparations of purity between 98.5 and 100%.

A further subject of the invention is the purified preparations of diaminochlorotriazine. (DCT) obtained in this process.

This process makes it possible, in effect, to obtain a DCT of purity greater than 99.5%. The subject of the invention is hence also the DCT preparations having such a purity, in particular as intermediate products.

A further subject of the invention is the purified preparations of melarsen acid hydrochloride (MAH) obtained in the process of the invention.

This process makes it possible, in effect, to produce a MAH of purity greater than 99%. The subject of the invention is hence also the MAH preparations having such a purity, in particular as intermediate products.

The subject of the invention is also the purified preparations of melarsen oxide dihydrate obtained in the process of the invention.

This process makes it possible, in effect, to produce a melarsen oxide dihydrate of purity greater than 99%. The subject of the invention is hence also the melarsen oxide dihydrate preparations having such a purity, in particular as intermediate products.

Figure 1:
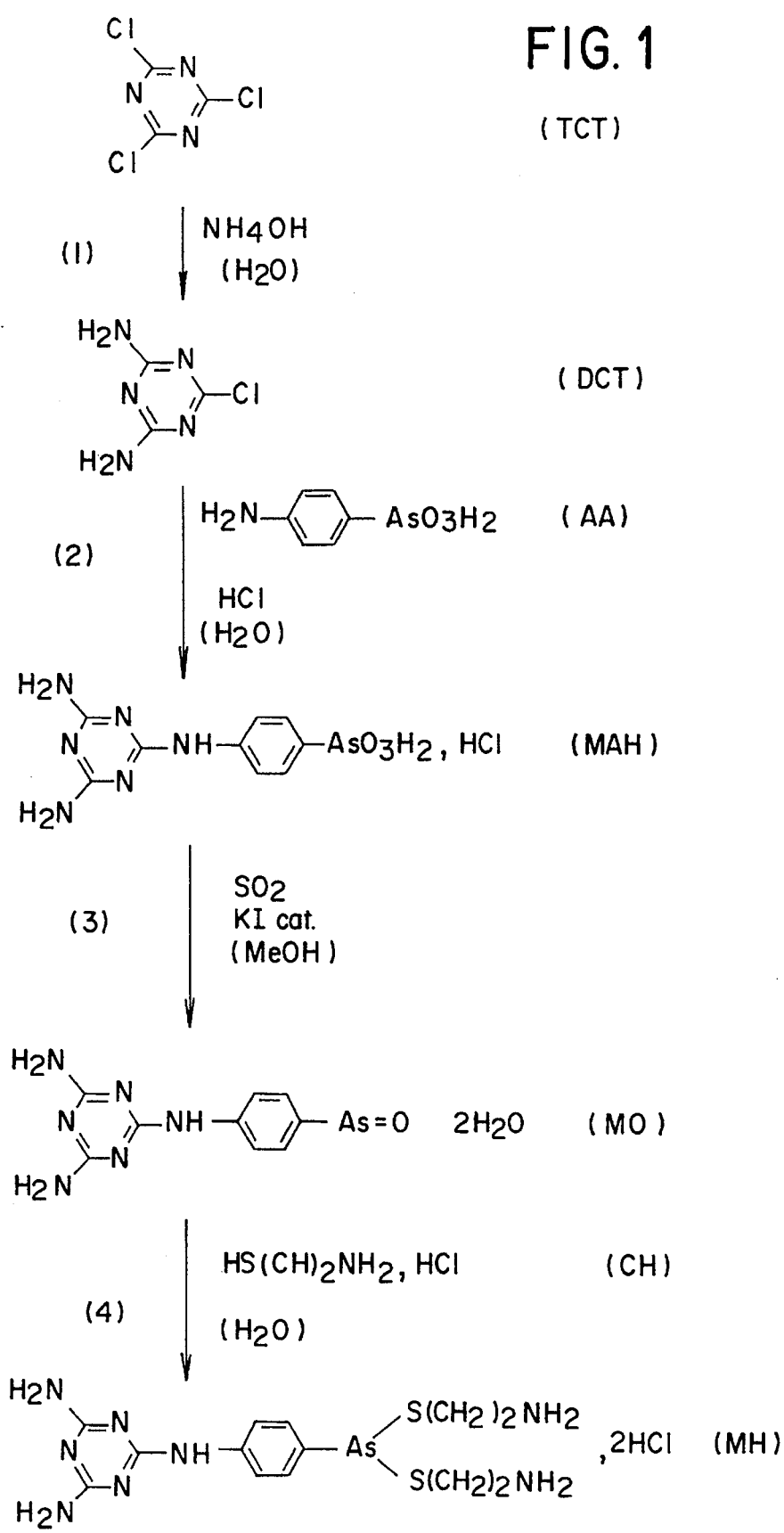
FIG. 1. is a schematic diagram of the steps of the invention.

The invention will now be described in greater detail below. Reference may be made to FIG. 1, illustrating diagrammatically in a general manner the steps of the process according to the invention. The abbreviations therein have the following meanings:

TCT: trichlorotriazine
DCT: diaminochlorotriazine
AA: arsanilic acid
MAH: melarsen acid hydrochloride
MO: melarsen oxide dihydrate
CH: cysteamine hydrochloride
MH: melarsomine dihydrochloride.

Figure 2:
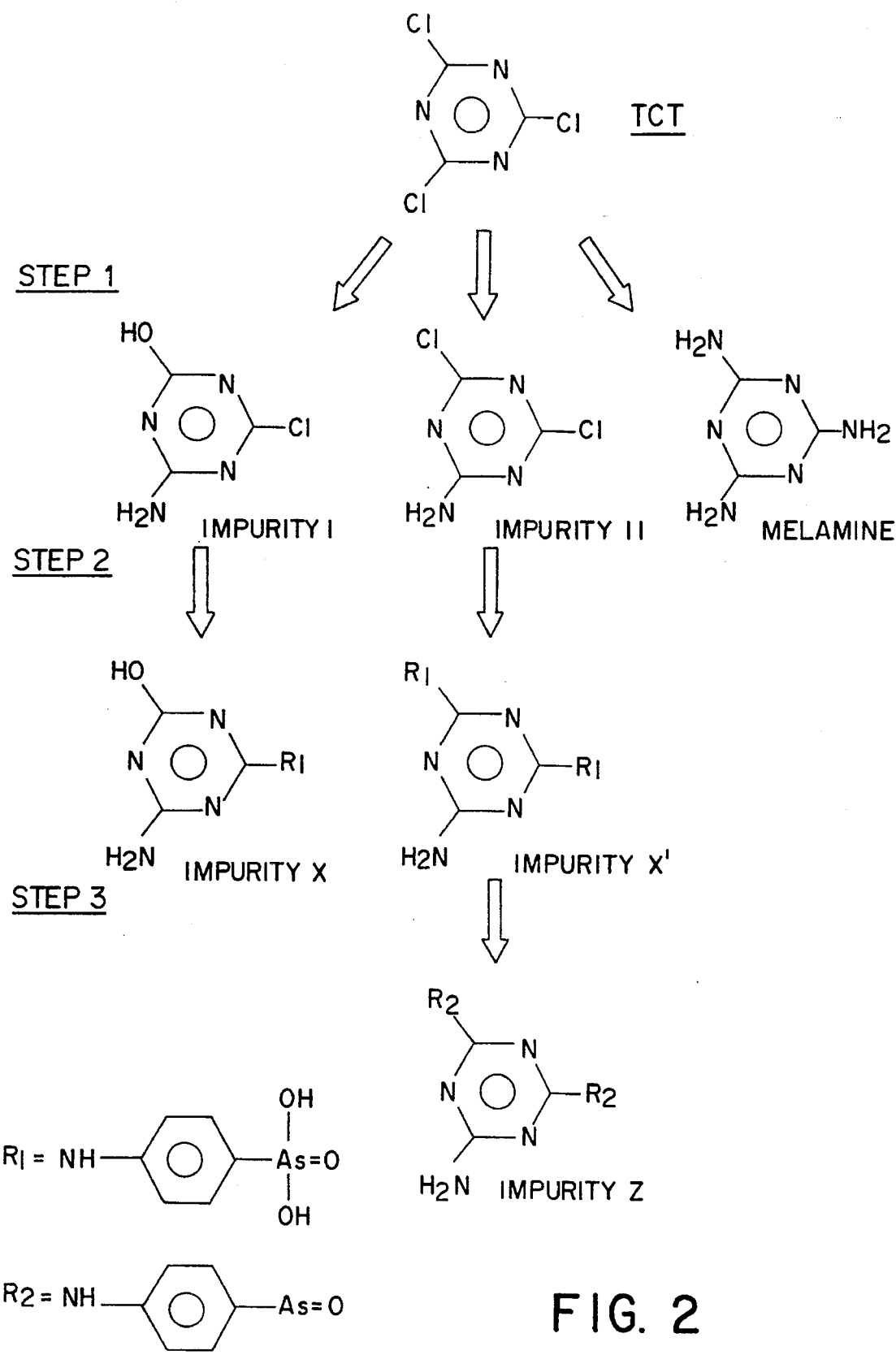
FIG. 2. is a schematic diagram showing the impurities which may be produced during steps 1, 2, and 3 of the invention.

FIG. 2 shows the impurities (impurities I, II X, X', Z and melamine) which may be produced during steps 1, 2 and 3 of the process, and identifies them by their structural formulae.

Assay of diaminochlorotriazine: reverse-phase high pressure liquid chromatography in comparison with a reference series.

Assay of melarsen acid hydrochloride: high pressure liquid chromatography in comparison with an arsanilic acid and melarsen acid series.

Assay of melarsen oxide dihydrate: high pressure liquid chromatography in comparison with a melarsen oxide and melarsen acid series.

Assay of melarsomine dihydrochloride: ultraviolet adsorption spectrophotometry in comparison with a reference series, and high pressure liquid chromatography in comparison with a melarsomine dihydrochloride reference.

Step 1. Production of 2-chloro-4,6-diaminotriazine.

Examples 1 and 2 below do not follow the conditions of the invention. They are given by way of comparison.

Comparative Example 1

The whole of the TCT charge (Fluka commercial product, product no. 28620, purity>98% ) is added to the ammonia solution at 20 ° C. The temperature of the reaction medium rapidly rises to 75° C. The trichlorotriazine concentration is 150 g/kg. The reaction time is 1 hour.

The finished product contains two impurities, the percentages of which are 15.4% for I and 8.2% for II respectively. The formulae of I and II are given in FIG. 2.

The phases of purification in water at 20° C. and 95 ° C. did not enable the contents of impurities to be lowered to less than 4%.

Melamine is formed (FIG. 2), but is removed by washing with water.

Comparative Example 2

TCT is added during 20 min to an ammonia solution at 9° C. The temperature of the reaction medium rises from 9° to 30 ° C. The concentration of trichlorotriazine in suspension is 193 g/l. When the addition is complete, the temperature falls to 20° C., and is then raised to 45° C. and maintained at this value for 1 h 30 min.

The contents of impurities are 0.6% for I and 6.5% for II. Purification with water enables the level of impurity II to be lowered to 3.5%.

Example 3

TCT is added during 40 rain to an ammonia solution at 4° C. The temperature of the reaction medium rises from 4° to 11° C. and is maintained below 12° C. for 4 hours. The final concentration of trichlorotriazine equivalent in suspension is 6.5 g/l. The temperature of the medium then raised to 38° C. and maintained for 210 minutes. The contents of impurities are 3.2% for I and 2.8% for II. Purification with water enables the levels of I to be lowered to 0.6% and of II to 1.8%.

Example 4

TCT is added during 40 min to an ammonia solution at 10° C., in which it occurs in suspension. The temperature of the reaction medium never exceeds 13° C. throughout the addition. When the addition is complete, the temperature of the medium is brought to 40° C. and then maintained for 1 hour. The final concentration of TCT equivalent (suspended solid) is 65 g/l. The solid is then purified in water at 90° C. for 1 hour. The contents of impurities are 0.1% for I and 0.4% for II.

Example 5

TCT is added during 120 min in 4 steps to an ammonia solution at 4° C. Throughout the addition period, the temperature of the reaction medium does not exceed 4° to 5° C. The medium is then heated to 40° C. with maintenance of this temperature for 90 minutes. The concentration of trichlorotriazine equivalent is 60 g/l. The wet solid obtained is purified in water at 90°–95° C. The impurities I and II are no longer detected and lie at values relative to contents below 0.1%.

Step 2.

The wet or dry and ground 2-chloro-4,6-diaminotriazine is used to synthesise melarsen acid hydrochloride from p-arsanilic acid (SIGMA commercial product, no. A 9268, purity>99%). The reaction which takes place at between 0° and 95° C. in an aqueous medium is finished when dissolution is complete. The MAH is precipitated by adding a hydrochloric acid solution. The level of impurities in the melarsen acid hydrochloride is dependent on the degree of purity of the 2-chloro-4,6-diaminotriazine (DCT).

With the DCT of Example 1, the percentage of impurities is 0.4% for X and 4% for X' (see FIG. 2).

With the DCT of Example 4, X is 0.3% and X' is 0.2%.

Step 3:

Example 6

Methanol ( kg/kg MAH): 6.4
KI (kg/kg MAH): 0.032
HCl, 35–37% (kg/kg MAH): 0.19
Temperature: 30° C.
$SO_2$ ( kg/kg MAH): 0.485
Time of $SO_2$ injection: 1 to 2 h
$SO_2$ flow rate (kg/kg MAH/h): 0.320
Reaction time: 5 to 25 h
Water: 24 l
Sodium hydroxide, 30.5% (1/kg MAH): 1.4
Purification stages: none
Volume of mother liquors (1/kg MAH): 50 to 60
Yield: 90 to 95%

This process is characterised by a low consumption of KI and of $SO_2$, which has greater solubility in methanol than in water. It is, furthermore, injected into the reaction medium, which improves gas-liquid transfer and hence the kinetics.

At the end of the reaction in methanol, the medium is clear, enabling the end of the reaction to be assessed. The absence of a purification phase is reflected very positively in the productivity and yield of the reaction and limits considerably the volume of mother liquors.

The melarsen oxide is precipitated in the aqueous-alcoholic phase at between pH 8 and 10, and preferably at pH 9, with sodium hydroxide.

Example 7

200 ml of methanol, 25 g of dry roelarsen acid and 0.8 g of KI are placed in a 250-ml reactor. The medium is heated to 30° C. and the temperature is maintained at this value throughout the reaction. 14.6 g of sulphur dioxide are injected in the course of 1 h 30 min into the methanolic solution, which is stirred using a turbo-mixer. The degrees of conversion of melarsen acid hydrochloride to melarsen oxide are 0.47 in 270 min and 0.98 in 1,320 min. The melarsen oxide is precipitated under the same conditions as in Example 6.

Example 8

100 ml of methanol, 25 g of dry melarsen acid, 0.8 g of KI and 4 ml of 35% hydrochloric acid are placed in a 250-ml reactor. The medium is heated to 40° C. and maintained at this value throughout the reaction. 15 g of sulphur dioxide are injected in the course of 1 h 30 min. The degrees of conversion are 0.93 in 270 min and 0.97 in 1,320 min. The melarsen oxide is precipitated as above.

Example 9

200 ml of methanol, 25 g of dry melarsen acid, 0.8 g of KI and 4 ml of 35% hydrochloric acid are placed in a 250-ml reactor. The medium is heated to 30° C. and the temperature is maintained at this value throughout the reaction. 12 g of sulphur dioxide are injected in the course of 1 h 30 min-into the methanolic solution, which is stirred according to Example 7. The degrees of conversion of melarsen acid hydrochloride to roelarsen oxide are 0.94 in 270 min and 0.99 in 1,320 min. The roelarsen oxide is precipitated as above.

The products derived from Examples 1 and 4, converted to melarsen acid hydrochloride, were treated according to Example 9 to give two samples 1' and 4' of melarsen oxide dihydrate. 1' contains 3% of an impurity Z, and 4', 0.2% of the same impurity Z (see FIG. 2).

Example 10

Process of Example 9, without iodine. The reaction is slower.
Step 4.
The reaction is performed on the basis of approximately 1 mol of melarsen oxide dihydrate per 2 mol of cysteamine hydrochloride:

Example 11

1 kg of melarsen oxide dihydrate is dispersed in a solution of cysteamine hydrochloride (FLUKA, Aldrich) at a concentration of 0.83 kg/kg of water, which is stirred.

0.5 kg of water is added and the temperature of the reaction is maintained at 40° C. until dissolution has taken place.

The solution obtained is cooled to +0° C. and seeded with stirring with a batch of melarsomine dihydrochloride in order to initiate crystallisation.

After 10 to 20 hours, the solid is recovered and then washed with 3 litres of ethanol.

After drying at 60° C. for between 10 and 20 hours, the purities of the melarsomine dihydrochloride preparations obtained from 1' and 4' are 96.8% and 100%, respectively.

As a variant, it is also possible to suspend 1 kg of melarsen oxide dihydrate in 0.5 kg of water, and then to add the cysteamine hydrochloride solution.

We claim:

1. Process for the synthesis of cysteamine melaminylthioarsenate dihydrochloride or melarsomine dihydrochloride, comprising:

step 1: converting trichlorotriazine (TCT) to diaminochlorotriazine (DCT) by gradual addition of TCT in an ammoniacal medium;

step 2: converting the DCT to melarsen acid hydrochloride (MAH) in the presence of arsanilic acid;

step 3: reducing the MAH to melarsen oxide dihydrate, by reaction of MAH in an aqueous, aqueous-alcoholic or organic medium then followed by precipitation to recover the melarsen oxide; and step 4: converting the melarsen oxide dihydrate to melarsomine dihydrochloride in the presence of cysteamine hydrochloride in an aqueous medium.

2. Process according to claim 1, wherein, in step 1, the TCT is reacted with an ammonia solution in two substeps, the first comprising the gradual addition of TCt to the ammoniacal medium comprising an excess of ammonia with respect to TCT under conditions that limit the reaction temperature to below approximately 20° C., and preferably to a temperature of the order of 0° to 5° C., throughout this first substep, while, in the second substep, the reaction is completed by bringing the temperature of the solution obtained to between 20° and 90° C., and the diaminochlorotriazine (DCT) obtained is then purified by washing with hot water.

3. Process according to claim 2, characterised in that:

in step 2: in an aqueous medium, the DCT is converted to melarsen acid hydrochloride (MAH) in the presence of arsanilic acid, and the MAH is then precipitated in an acid medium;

in step 3: the melarsen acid hydrochloride, previously dried or otherwise, is reduced in an aqueous, an aqueous-alcoholic or an organic medium, in the presence of a reducing agent and optionally of traces of potassium iodide, to give melarsen oxide dihydrate; and in step 4: the dry or wet melarsen oxide dihydrate is suspended in water and then brought into contact with cysteamine hydrochloride to give melarsomine dihydrochloride, which may thereafter be recovered in solid form by crystallisation at low temperature or the like, followed by drying.

4. Process according to claim 3, characterised in that:

step 2 is performed at a temperature of between 0° and 95° C., until dissolution of the arsanilic acid is complete;

step 3 is performed at a temperature of the order of 10° to 60° C., with a gradual injection of $SO_2$ as reducing agent in the proportion of 4.4 to 20 g of $SO_2$ per 25 g of melarsen acid, the reaction being continued until a homogeneous medium is obtained;

step 4 is carried out at a temperature of between 20° and 100° C. until dissolution of the melarsen oxide dihydrate is complete.

5. Process according to claim 3, characterised in that step 3 is performed in a volume of 100 to 200 ml of methanol per 10 to 60 g of dry or wet melarsen acid.

6. Process according to claim 1, characterised in that the melarsen oxide dihydrate is precipitated in the aqueous-alcoholic phase at between pH 8 and 10 with sodium hydroxide.

7. Process according to claim 2, characterised in that, in step 1, from 30 to 200 g of TCT are reacted per liter of ammonia solution.

8. Process according to claim 2, characterised in that TCT is introduced over a period of more than 40 min, in continuous or discontinuous fashion, into the ammonia solution whose initial temperature is between 0° and 20° C.

9. Process according to claim 3, characterised in that, in the second substep of step 1, the solution is heated to between 20° and 90° C. for from 10 to 180 min.

10. Process according to claim 2, characterised in that the DCT obtained in step 1 is purified by suspension in water at 90°–95° C. approximately.

11. Process according to claim 3, characterised in that step 4 is performed with approximately 1 mol of melarsen oxide dihydrate per 2 mol of cysteamine hydrochloride.

12. Process according to claim 1, wherein, in step 1, the ammoniacal medium comprises initially an excess of ammonia with respect to the TCT.

13. Process according to claim 1, wherein, in step 3, the reaction is conducted in an organic medium selected from the group consisting of tertiary butanol, isopropanol, ethanol and methanol.

14. Process according to claim 1, wherein step 3 is carried out with methanol as organic medium.

15. Process according to claim 2, wherein, in step 3, the MAH is reduced by $SO_2$ as reducing agent.

* * * * *